United States Patent
Hong et al.

(10) Patent No.: US 10,596,017 B2
(45) Date of Patent: Mar. 24, 2020

(54) SELF-SEALING TUBULAR GRAFTS, PATCHES, AND METHODS FOR MAKING AND USING THEM

(71) Applicant: Solinas Medical Inc., Santa Clara, CA (US)

(72) Inventors: James Hong, Santa Clara, CA (US); Erik van der Burg, Los Gatos, CA (US); Amy Lee, Sunnyvale, CA (US)

(73) Assignee: SOLINAS MEDICAL INC., Santa Clara, CA (US)

( * ) Notice: Subject to any disclaimer, the term of this patent is extended or adjusted under 35 U.S.C. 154(b) by 178 days.

(21) Appl. No.: 15/494,254

(22) Filed: Apr. 21, 2017

(65) Prior Publication Data
US 2017/0304092 A1   Oct. 26, 2017

Related U.S. Application Data

(60) Provisional application No. 62/327,328, filed on Apr. 25, 2016, provisional application No. 62/471,867, filed on Mar. 15, 2017.

(51) Int. Cl.
*A61F 2/89* (2013.01)
*A61F 2/07* (2013.01)
(Continued)

(52) U.S. Cl.
CPC .................. *A61F 2/89* (2013.01); *A61F 2/06* (2013.01); *A61F 2/07* (2013.01); *A61F 2/82* (2013.01);
(Continued)

(58) Field of Classification Search
CPC ...... A61F 2/82; A61F 2/07; A61F 2/06; A61F 2002/072; A61M 1/3655; A61B 2017/3419
See application file for complete search history.

(56) References Cited

U.S. PATENT DOCUMENTS

| 3,814,137 A | 6/1974 | Martinez |
| 4,428,364 A | 1/1984 | Bartolo |
| (Continued) | | |

FOREIGN PATENT DOCUMENTS

| CN | 101384228 A | 3/2009 |
| EP | 1649888 | 4/2006 |
| (Continued) | | |

OTHER PUBLICATIONS

Korean Intellectual Property Office, International Search Report for corresponding International Application No. PCT/US2017028939, Applicant: Solinas Medical, Inc., Form PCT/ISA/210, dated Aug. 14, 2017, 4 pages.
(Continued)

*Primary Examiner* — Dinah Baria
(74) *Attorney, Agent, or Firm* — William A. English; Vista IP Law Group LLP

(57) ABSTRACT

A self-sealing tubular graft is provided for implantation within a patient's body that includes an elongate tubular body including first and second self-sealing cannulation regions and a loop region extending between the first and second cannulation regions. The loop region includes one or more reinforcement members attached to a first length of the loop region and extending at least partially around a circumference of the tubular body. For example, the reinforcement members may include one or more sinusoidal or zigzag members extending along the first length with alternating peaks and valleys extending at least partially around a circumference of the tubular body. Self-sealing patches are also provided that include one or more reinforcement members embedded within base material.

18 Claims, 19 Drawing Sheets

(51) Int. Cl.
*A61F 2/82* (2013.01)
*A61F 2/06* (2013.01)
*A61F 2/88* (2006.01)
*A61M 1/36* (2006.01)

(52) U.S. Cl.
CPC .............. *A61F 2/88* (2013.01); *A61M 1/3655* (2013.01); *A61F 2/885* (2013.01); *A61F 2002/072* (2013.01); *A61F 2230/0069* (2013.01)

(56) References Cited

U.S. PATENT DOCUMENTS

| | | |
|---|---|---|
| 4,564,915 A | 1/1986 | Evans et al. |
| 4,619,641 A | 10/1986 | Shanzer |
| 4,645,495 A | 2/1987 | Vaillan-court |
| 4,816,339 A | 3/1989 | Tu et al. |
| 5,100,422 A | 3/1992 | Berguer et al. |
| 5,342,387 A * | 8/1994 | Summers ............... A61F 2/88 606/198 |
| 5,562,617 A | 10/1996 | Finch, Jr. et al. |
| 5,647,855 A | 7/1997 | Trooskin |
| 5,713,859 A | 2/1998 | Finch, Jr. et al. |
| 5,755,769 A | 5/1998 | Richard et al. |
| 5,800,512 A | 9/1998 | Lentz |
| 5,866,217 A | 2/1999 | Stenoien et al. |
| 5,906,596 A | 5/1999 | Tallarida |
| 5,931,865 A | 8/1999 | Silverman et al. |
| 5,944,688 A | 8/1999 | Lois |
| 5,984,955 A | 11/1999 | Wisselink |
| 6,007,516 A | 12/1999 | Burbank |
| 6,149,681 A | 11/2000 | Houser et al. |
| 6,261,257 B1 | 7/2001 | Uflacker et al. |
| 6,319,279 B1 | 11/2001 | Shannon |
| 6,436,135 B1 | 8/2002 | Goldfarb |
| 6,553,167 B2 | 4/2003 | Hurley et al. |
| 6,582,409 B1 | 6/2003 | Squitieri |
| 6,645,242 B1 | 11/2003 | Quinn |
| 6,790,225 B1 | 9/2004 | Shannon et al. |
| 6,962,577 B2 | 11/2005 | Tallarida et al. |
| 7,056,336 B2 | 6/2006 | Armstrong |
| 7,255,682 B1 | 8/2007 | Bartol et al. |
| 7,261,705 B2 | 8/2007 | Edoga et al. |
| 7,438,721 B2 | 10/2008 | Doig |
| 7,452,374 B2 | 11/2008 | Hain |
| 7,727,143 B2 | 6/2010 | Birk et al. |
| 7,762,977 B2 | 7/2010 | Porter et al. |
| 7,780,590 B2 | 8/2010 | Birk et al. |
| 7,914,438 B2 | 3/2011 | Buckberg et al. |
| 8,079,973 B2 | 12/2011 | Herrig et al. |
| 8,163,002 B2 | 4/2012 | Weinberg |
| 8,313,524 B2 | 11/2012 | Edwin et al. |
| 8,414,530 B2 | 4/2013 | Mason |
| 8,906,087 B2 | 12/2014 | House et al. |
| 2002/0188318 A1 | 12/2002 | Carley et al. |
| 2003/0100920 A1 | 5/2003 | Akin et al. |
| 2005/0131520 A1 | 6/2005 | Zilla et al. |
| 2006/0025848 A1 | 2/2006 | Weber et al. |
| 2006/0281966 A1 | 12/2006 | Peacock |
| 2007/0088336 A1 | 4/2007 | Dalton |
| 2007/0123968 A1 | 5/2007 | Weinberg |
| 2007/0167901 A1 | 7/2007 | Herrig et al. |
| 2007/0213838 A1 | 9/2007 | Hengel-molen |
| 2007/0265584 A1 | 11/2007 | Hickman et al. |
| 2007/0299538 A1 | 12/2007 | Roeber |
| 2008/0009889 A1 | 1/2008 | Pokorney et al. |
| 2008/0243080 A1 | 10/2008 | Chang |
| 2009/0157014 A1 | 6/2009 | Osborne et al. |
| 2010/0292774 A1 | 11/2010 | Shalev |
| 2011/0295181 A1 | 12/2011 | Dann et al. |
| 2012/0058249 A1 | 3/2012 | House et al. |
| 2012/0310324 A1 | 12/2012 | Benary et al. |
| 2013/0060268 A1 | 3/2013 | Herrig |
| 2013/0090723 A1 | 4/2013 | Cully et al. |
| 2013/0237929 A1* | 9/2013 | Hong ............... A61B 17/0057 604/264 |
| 2014/0180190 A1 | 6/2014 | Dann et al. |
| 2015/0025437 A1 | 1/2015 | Tomko et al. |
| 2015/0327844 A1 | 11/2015 | Hong et al. |
| 2016/0199085 A1 | 7/2016 | Hong et al. |

FOREIGN PATENT DOCUMENTS

| | | |
|---|---|---|
| WO | 9846115 A2 | 10/1998 |
| WO | 2007061787 A2 | 5/2007 |
| WO | 2010015001 | 2/2010 |

OTHER PUBLICATIONS

Korean Intellectual Property Office, Written Opinion for corresponding International Application No. PCT/US2017028939, Applicant: Solinas Medical, Inc., Form PCT/ISA/237, dated Aug. 14, 2017, 8 pages.

* cited by examiner

SELF-SEALING TUBULAR GRAFTS, PATCHES, AND METHODS FOR MAKING AND USING THEM

RELATED APPLICATION DATA

This application claims benefit of U.S. provisional application Ser. Nos. 62/327,328, filed Apr. 25, 2016, and 62/471,867, filed Mar. 15, 2017, the entire disclosures of which are expressly incorporated by reference herein.

STATEMENT REGARDING FEDERALLY SPONSORED RESEARCH AND DEVELOPMENT

This invention was made with Government support under SBIR Grant Nos. 1143198 and 1329172 awarded by the National Science Foundation. The Government has certain rights in the invention.

FIELD OF THE INVENTION

The field of the invention generally relates to self-sealing devices that are implantable within a patient's body and to apparatus, systems, and methods including such self-sealing devices. For example, the present invention may include self-sealing grafts, self-sealing patches for tubular or other structures that include resealable access regions and/or methods for making and implanting such self-sealing grafts or patches.

BACKGROUND

Dialysis for end stage renal disease ("ESRD") is one of the leading and rapidly growing problems facing the world today. In 2006, there were greater than fifty one million (51,000,000) people in the United States diagnosed with chronic kidney disease. Greater than five hundred thousand (500,000) people in this population suffered from ESRD. With the growing aging population and increasing prevalence of high risk factors such as diabetes (35% of all ESRD patients, Szycher M., *J Biomater Appl.* 1999; 13, 297-350) and hypertension (30%), the projected population in 2020 is greater than seven hundred eighty four thousand (784,000) (est. USRDS 2008).

The two primary modes of treatment are kidney transplant and hemodialysis. Due to the shortage of available transplant kidneys, approximately seventy percent (70%) of people with ESRD undergo hemodialysis (USRDS 2008) for life or until a transplant kidney becomes available. To facilitate the frequent, periodic treatments, patients must undergo vascular surgery to prepare their artery and vein, typically in their forearms, for dialysis. The two most common methods of preparing the artery and vein are arteriovenous (AV) fistulas and AV grafts—the former is the preferred option due to longer patency rates; however fistulas are often replaced by AV grafts once the life of the fistula has been exhausted.

There are advantages and disadvantages to both methods. Most notably, grafts are easy to implant, and ready to use relatively sooner, but have shorter lifespans and are more prone to infection and thrombus formation. Fistulas have greater durability and are less prone to infection, but can take up to six (6) months (KDOQI) to mature before use, and the veins used for access have tendencies to develop pseudo-aneurysms at the site of repeated access. One of the contributing factors to the rapid degradation of current AV grafts and/or veins is the repeated needle sticks during dialysis with relatively large needles (e.g., 14-16 Gauge). This is exacerbated because the average patient undergoes hemodialysis treatment two or three times a week, every week of every year until a kidney replacement is available or until the end of their life expectancy, which is approximately ten (10) years (Szycher M., *J Biomater Appl.* 1999; 13, 297-350). Moreover, due to the high risk of intimal hyperplasia and vessel narrowing, dialysis patients also undergo periodic interventional treatment to maintain patent vessels, which may occur several times a year. This typically involves angioplasty or stenting, akin to the treatment of coronary vascular occlusions, and vascular access using needles is also needed for these procedures, thereby contributing to the risk of graft or vessel degradation.

Therefore, there is an apparent need for devices, systems, and methods for treating ESRD and other conditions.

SUMMARY

The present application generally relates to self-sealing devices that are implantable within a patient's body and to apparatus, systems, and methods including such self-sealing devices. For example, the present invention may include self-sealing grafts or self-sealing patches for tubular or other structures that include resealable access regions and/or methods for making and implanting such self-sealing grafts and patches.

In accordance with an exemplary embodiment, a tubular graft is provided that includes an elongate tubular body including a first end, a second end, and a lumen extending between the first and second ends, the tubular body including a first cannulation region adjacent the first end, a second cannulation region adjacent the second end, and a loop region extending between the first and second cannulation regions. A first self-sealing member including one or more reinforcement members embedded within a base material at least partially surrounds the first cannulation region, a second self-sealing member including one or more reinforcement members embedded within a base material at least partially surrounds the second cannulation region; and one or more loop region reinforcement members are attached to a first length of the loop region that extend at least partially around a circumference of the tubular body.

In accordance with another exemplary embodiment, a tubular graft is provided that includes an elongate tubular body including a first end, a second end, and a lumen extending between the first and second ends; and a first self-sealing region at least partially surrounding a first length of the tubular body, the self-sealing region including one or more reinforcement members embedded within a base material, the one or more reinforcement members comprising a first zigzag member that extends axially along the first length and includes alternating loops defining peaks and valleys that extend at least partially around a circumference of the tubular body.

In accordance with still another embodiment, a tubular graft is provided that includes an elongate tubular body including a first end, a second end, and a lumen extending between the first and second ends; and a first self-sealing region at least partially surrounding a first length of the tubular body, the self-sealing region including one or more reinforcement members embedded within a base material, the one or more reinforcement members comprising a first helical coil that extends axially along the first length, the helical coil applying an axially compressive force to the base material.

In accordance with yet another embodiment, a tubular graft is provided that includes an elongate tubular body including a first end, a second end, and a lumen extending between the first and second ends; and a first self-sealing region at least partially surrounding a first length of the tubular body, the self-sealing region including first and second reinforcement members embedded within a base material, the first reinforcement member extending axially along the first length and including elements that extend at least partially around a circumference of the tubular body, the second reinforcement member extending axially along the first length and including elements that extend at least partially around a circumference of the tubular body, the second reinforcement member spaced apart radially from the first reinforcement member.

Other aspects and features of the present invention will become apparent from consideration of the following description taken in conjunction with the accompanying drawings.

BRIEF DESCRIPTION OF THE DRAWINGS

The drawings illustrate exemplary embodiments, in which.

DETAILED DESCRIPTION OF THE EXEMPLARY EMBODIMENTS

Figure 1:
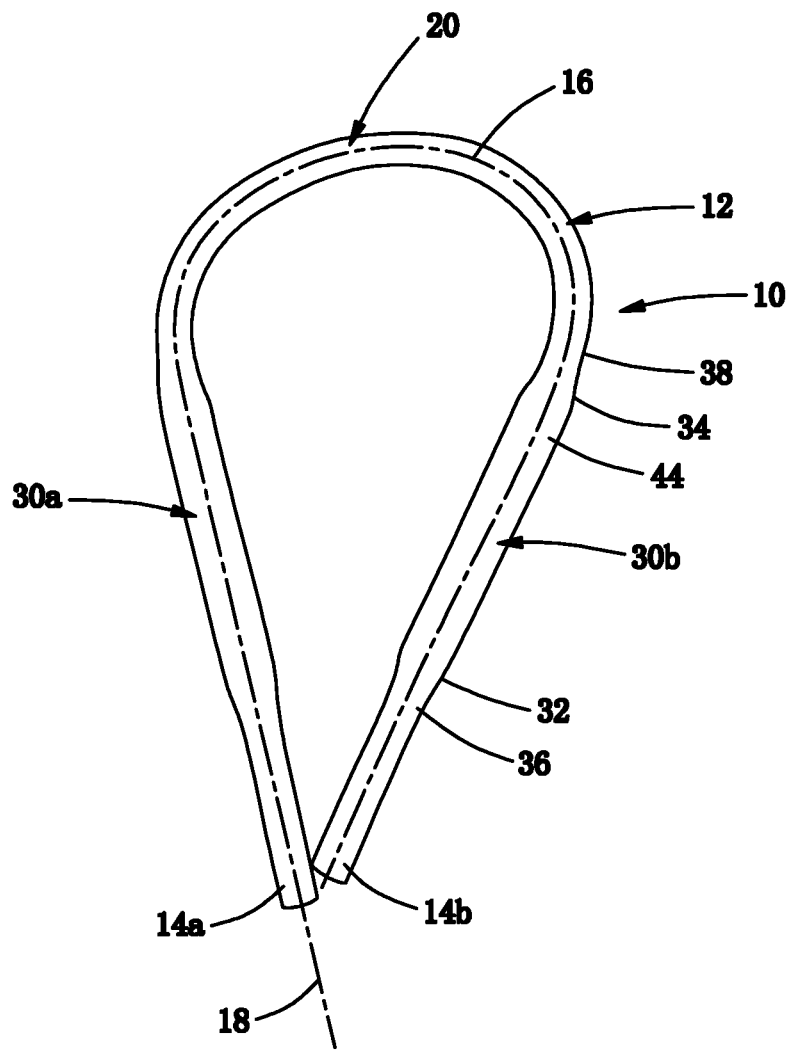
FIG. 1 is a perspective view of an exemplary embodiment of a tubular graft including two self-sealing cannulation regions and a loop region between the cannulation regions.
Figure 2A:
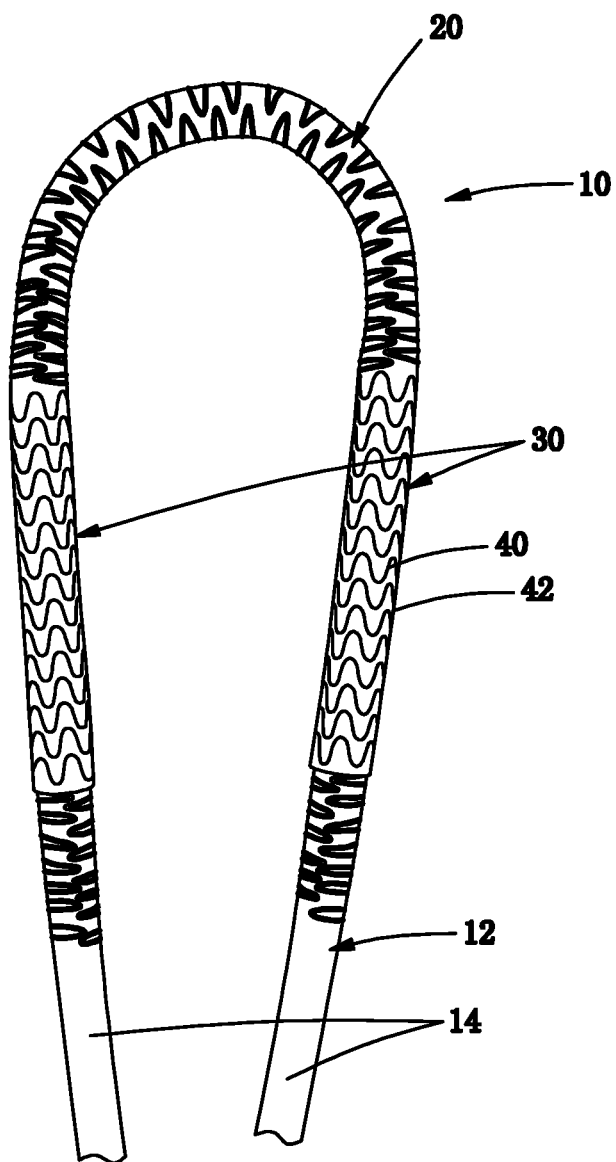
FIGS. 2A and 2B are details of the tubular graft of FIG. 1 showing one or more reinforcement elements around the loop region and one or more embedded reinforcement elements along the cannulation regions before applying an outer layer over the cannulation regions (FIG. 2A) and after applying the outer layer (FIG. 2B).
Figure 2B:
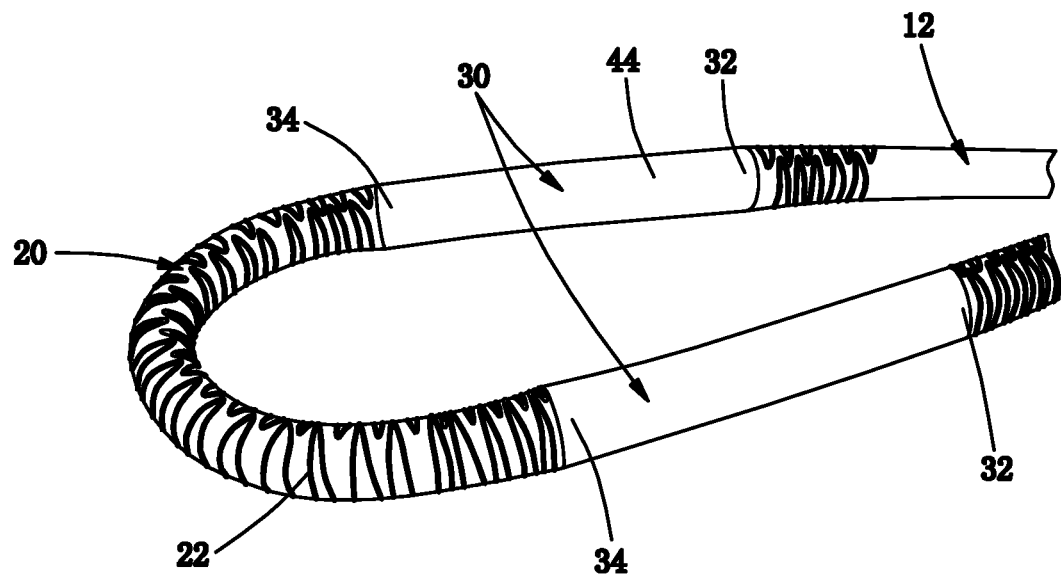

Turning to the drawings, FIGS. 1-2B show an exemplary embodiment of a tubular graft 10 that includes an intermediate loop region 20 and a pair of self-sealing cannulation regions 30 on either side of the loop region 20, e.g., configured to allow the tubular graft 10 to be punctured with a needle, cannula, and/or other device (not shown) to allow access into the graft 10. In addition or alternatively, the cannulation regions 30 may provide access during other procedures, e.g., angioplasty, vascular stenting, or thrombectomy procedures, e.g., to manage and maintain AV patency for dialysis. In another alternative, the graft 10 may include only one cannulation region, if desired for a particular application, e.g., similar to the embodiments shown in FIGS. 6C-6D, 7A-7C, and 8A-8C, and described further elsewhere herein.

Generally, the graft 10 includes an elongate tubular graft body 12 including first and second ends 14a, 14b and a lumen 16 extending between the ends 14a, 14b, i.e., from the first end 14a along the first cannulation region 30a, the loop region 20, and the second cannulation region 30b to the second end 14b, thereby defining a central longitudinal axis 18 extending between the ends 14a, 14b. The graft body 12 may be fabricated from well-known synthetic or biological material for tubular grafts, e.g., a porous or nonporous material, such as ePTFE.

The graft 10 may be sized for implantation within a patient's body, e.g., within an arm of a patient (not shown) to provide an arteriovenous graft allowing arterial and venous access during hemodialysis. In exemplary embodiments, the lumen 16 may have an inner diameter between about one and forty millimeters (1-40 mm) or between about four and twenty millimeters (4.0-20 mm), and an overall length between the ends 14a, 14b between about five and eighty centimeters (5.0-80 cm).

As best seen in FIG. 2A, the cannulation regions 30 may be substantially straight regions located adjacent the ends 14a, 14b that include one or more reinforcement elements 40 embedded within a base material 42 and attached over or formed directly on desired lengths of the graft body 12. Optionally, as shown in FIGS. 1 and 2B, an outer layer of material, e.g., a sleeve of polymeric material, such as ePTFE, may be provided over the reinforcement elements 40 and base material 42, e.g., between first and second ends 32, 34, of each cannulation region 30, and/or a transition region 36, 38 may be provided at each end 32, 34 tapering to the underlying graft body 12, e.g., to reduce the risk of the graft body 12 kinking immediately adjacent the cannulation regions 30. In exemplary embodiments, each cannulation region 30 may be offset a desired distance from the respective end 14, e.g., between about one and thirty centimeters (1.0-30 cm) or between about one and ten centimeters (1.0-10 cm), and may have a length between about one and twenty centimeters (1.0-20 cm) and a wall thickness between about 0.3 and five millimeters (0.3-5.0 mm).

In an exemplary embodiment, each cannulation region 30 generally includes a plurality of reinforcement elements, e.g., a plurality of zigzag elements 40, e.g., formed from Nitinol or other elastic, superelastic, or shape memory material, embedded within or surrounding base material 42, e.g., silicone or other elastomeric material. The base material 42 may be substantially non-porous, i.e., may prevent fluid flow through the wall of the cannulation region 30, while, optionally, permitting tissue ingrowth, e.g., allowing surrounding tissue to grow into and/or otherwise engage the outer wall of the cannulation region 30. The reinforcement elements 40 may extend circumferentially around the graft body 12, e.g., as shown in FIG. 2A, and/or axially along the graft body 12 (not shown) for the desired length of the cannulation region 30, e.g., between the first and second ends 32, 34. For example, the reinforcement elements 40 may be biased to a relaxed or low energy state but elastically deformable to accommodate a needle or other device being inserted through the cannulation region 30 into the lumen 16 of the tubular graft 10. Thus, when the device is removed, the reinforcement elements 40 may bias the base material 42 to return to its original orientation, thereby sealing any punctures through the cannulation region 30. Exemplary embodiments of reinforcement elements, base material, and/or methods for making structures that may be used for the cannulation regions 30 may be found in U.S. Publication Nos. 2013/0237929 and 2016/0199085, the entire disclosures of which are expressly incorporated by reference herein.

For example, in the embodiment shown in FIG. 2A, the reinforcement elements 40 may be annular bands formed from continuous rings or "C" shaped collars of Nitinol material, e.g., laser cut, mechanically cut, stamped, machined, and the like, from a tube, wire, or sheet, e.g., similar to embodiments described in the applications incorporated by reference herein. Each band may extend at least partially around the periphery of the graft body 12 transverse to the longitudinal axis 18. For example, each band may include a plurality of longitudinal struts extending longitudinally including opposing ends that are alternately connected to adjacent struts by curved circumferential connectors, struts, or elements, e.g., to define an enclosed, annular zigzag or other serpentine pattern. The longitudinal struts may extend substantially parallel to the longitudinal axis 18 or, alternatively, may extend diagonally or helically relative to the longitudinal axis 18 (not shown).

Alternatively, the reinforcement elements 40 may include struts, wires, or other elements that extend axially along the length of the cannulation region 30. For example, a plurality of substantially straight wires or other filaments (not shown) may be embedded within or otherwise fixed to the base material 42. The filaments may be spaced apart sufficiently to accommodate inserting a needle or other device (not shown) through the cannulation region 30, with the filaments moving laterally to accommodate the device passing therethrough and resiliently returning to their original configuration to substantially seal the cannulation region 30, similar to other embodiments herein. Alternatively, the filaments may include a sinusoidal, zigzag, helical, or other pattern that extends at least partially transversely while the filaments extend generally axially between the ends 32, 34 of the cannulation region 30 (also not shown), e.g., similar to other embodiments described elsewhere herein.

The material of the reinforcement elements 40 may be heat treated and/or otherwise processed to provide a desired finish and/or mechanical properties. For example, the bands shown in FIG. 2A may be heat treated such that the bands are biased to a desired relaxed diameter, e.g., slightly larger, substantially the same, or smaller than the outer diameter of the graft body 12, yet the bands may be resiliently deformable, e.g., laterally within the circumferential plane of the cannulation region 30 to accommodate receiving a needle or other instrument (not shown) between adjacent struts and/or bands.

For example, in one option, the reinforcement elements 40 may impose a substantially continuous radially inward compressive force on the adjacent base material, i.e., radially inwardly towards the underlying graft body 12, which may enhance sealing any passages created through the base material, similar to embodiments described in the applications incorporated by reference herein. To accomplish this, the reinforcement elements 40 may be shape set to define a diameter smaller than the outer diameter of the graft body 12 in a relaxed or low energy state, and the reinforcement elements 40 may be resiliently expanded to fit over the graft body 12, e.g., before or after being embedded in the base material 42. In another option, the reinforcement elements 40 may define a diameter larger than the outer diameter of the graft body 12, e.g., such that the reinforcement elements 40 are in a low energy state radially that does not apply a radial force inwardly against the graft body 12 when embedded within the base material 42.

Alternatively, the reinforcement elements 40 may impose a substantially continuous axial compressive force, e.g., similar to other embodiments described elsewhere herein, instead of or in addition to, a radially inward force. For example, the reinforcement elements 40 may be shape set to define a predetermined axial spacing between adjacent windings (e.g., zero or greater) in a relaxed or low energy state, and the reinforcement elements 40 may be resiliently axially stretched when positioned over the graft body 12, e.g., before or after being embedded in the base material 42, as described elsewhere herein.

Optionally, instead of the outer layer 44 shown in FIGS. 1 and 2B, fabric (not shown) may be applied over any exposed surfaces, e.g., over the outer and end surfaces of the cannulation region 30 if the base material 42 is formed directly around the graft body 12, e.g., with the reinforcement elements 40 embedded within the base material 42 at the same time. Alternatively, if the reinforcement elements 40 are embedded within the base material 42 before attachment to the graft body 12, fabric may be applied over the outer, inner, and end surfaces before attachment. In another option, the cannulation regions 30 may include one or more tactile elements, ferromagnetic elements, echogenic elements, and the like (not shown), e.g., to facilitate locating the cannulation regions 30 when the graft 10 is implanted subcutaneously or otherwise within a patient's body, such as those disclosed in the applications incorporated by reference herein.

With particular reference to FIGS. 2A and 2B, the loop region 20 also includes one or more reinforcement elements 22 attached or otherwise provided around the tubular graft 12 along a first length of the loop region 20. For example, as best seen in FIG. 2B, the reinforcement element(s) 22 may extend circumferentially and/or axially along the loop region 20 entirely from one cannulation region 30a to the other cannulation region 30b. Alternatively, the reinforcement element(s) 22 may extend only partially between the cannulation regions 30, e.g., along a first length corresponding to a bend of the loop region 20.

Figure 3:
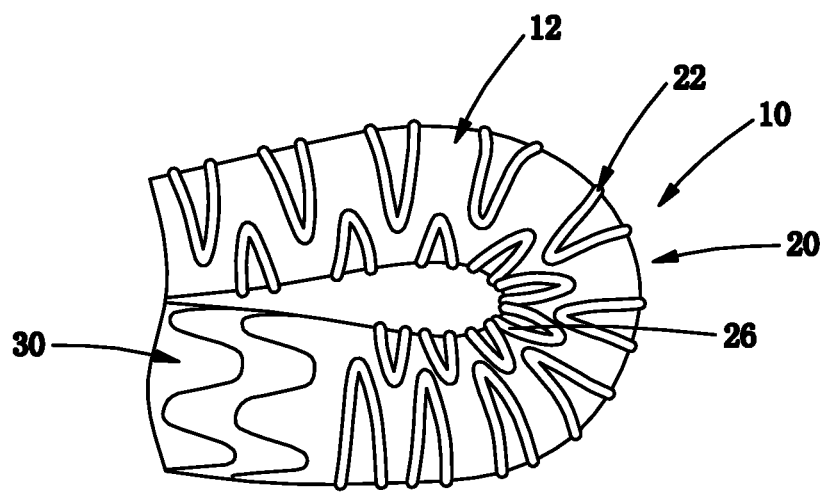
FIG. 3 is a detail of the loop region of the tubular graft of FIG. 1, showing the loop region bent into a tight radius with the reinforcement elements preventing kinking.

The reinforcement element(s) 22 may be formed from a variety of materials that provide predetermined hoop strength and/or otherwise support the underlying graft body 12 to prevent the material of the graft body 12 from being crushed, kinking, or buckling when the loop region 20 is positioned in a curved orientation. For example, as shown in FIG. 3, the loop region 20 may be bent or compressed into a tight loop, e.g., having a radius of curvature smaller than the diameter of the graft body 12; the reinforcement element(s) 22 may be attached to or otherwise support the graft body 12 to keep the lumen 16 substantially open even in such a small radius curve.

In an exemplary embodiment, the reinforcement element(s) 22 may be formed from thermoplastic materials, e.g., nylon, PTFE, or FEP, shape set to define a desired curved or circumferential shape having a radius similar to the outer diameter of the graft body 12. Alternatively, other materials may be used, e.g., Nitinol or other elastic or superelastic materials. The reinforcement element(s) 22 may have a desired cross-section, e.g., circular cross-section, an oval or elliptical cross-section, a square or rectangular cross-section, having a maximum width of between about 0.004-0.140 inch (0.1-3.5 mm), or not more than about 0.14 inch (3.5 mm).

The reinforcement element(s) 22 may be substantially permanently attached to the outer surface of the graft body 12, e.g., by bonding with adhesive, such as a silicone adhesive, fusing, sonic welding, and the like. In addition or alternatively, an external sleeve or other layer of material (not shown) may be positioned around and secured to or around the reinforcement element(s) 22, e.g., by interference fit, shrink fit, bonding, fusing, and the like. For example, in one embodiment, the reinforcement element(s) 22 may be applied around the graft body 12 without actually bonding to the graft body material (e.g., to create a pocket) and/or encapsulated around the graft body 12 to attach the reinforcement element(s) 22 to the underlying graft body 12.

In an exemplary embodiment, the reinforcement element(s) 22 may include one or more sinusoidal or other zigzag members 24, 124 including alternating loops (e.g., peaks 24a, 124a and valleys 24b, 124b) aligned along the longitudinal axis 18 of the first length. The zigzag member (s) 24, 124 may define a simple sinusoidal shape, e.g., as shown in FIGS. 4C and 5C, or may define a more complicated configuration of peaks and valleys, as desired. The alternating loops 24a, 124a, 24b, 124b may be shape set to extend at least partially around the circumference of the graft body 12. Thus, the loops 24a, 124a, 24b, 124b may define an arc orthogonal to the longitudinal axis 18 corresponding to an outer diameter of the graft body 12 with the arc length being a predetermined portion of the entire circumference, e.g., depending on the number of zigzag members 24, 124 and the desired circumferential coverage for the loop region 20.

Figure 4A:
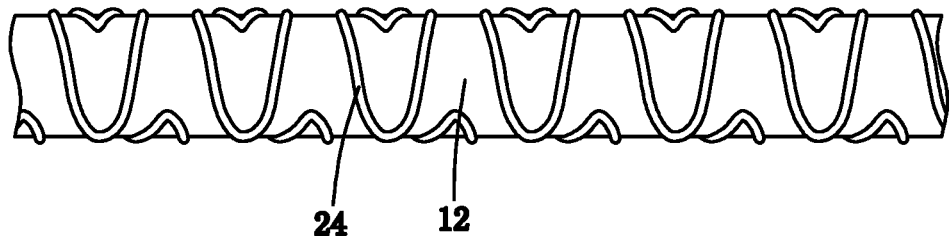
FIGS. 4A-4C are details showing an exemplary embodiment of reinforcement elements including two zigzag elements that extend along a loop region of a tubular graft, such as that of FIG. 1, with alternating loops of the zigzag elements wrapping partially around the circumference of the loop region.
Figure 4B:
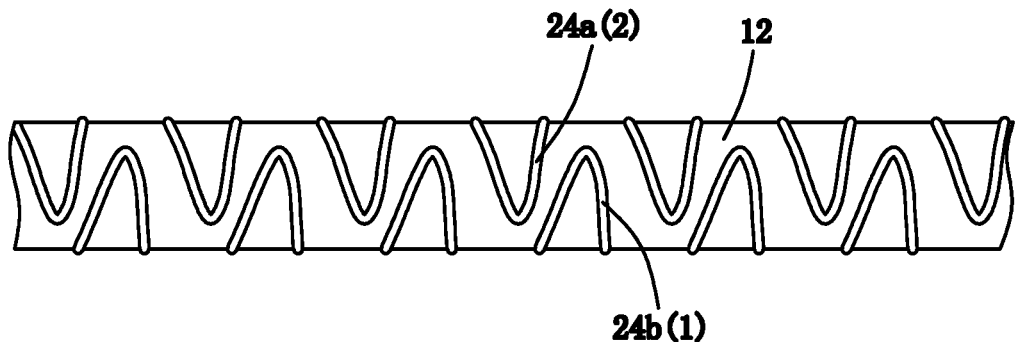
Figure 4C:
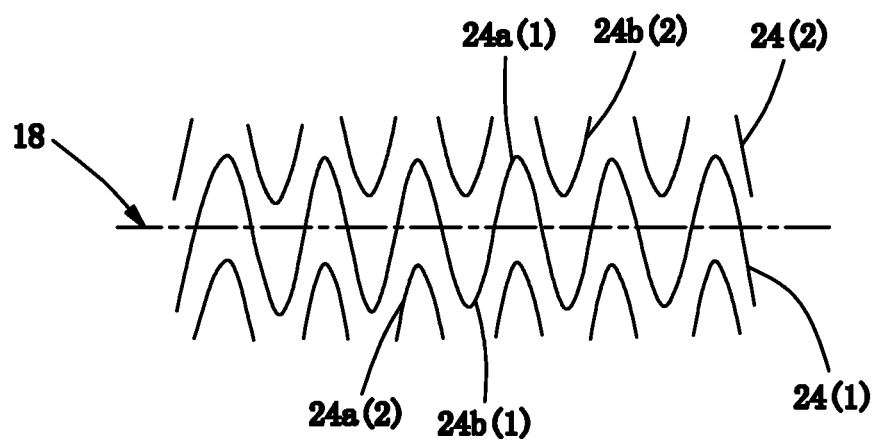

For example, FIGS. 4A-4D show an exemplary embodiment in which the reinforcement elements 24 include a pair of similar zigzag members 24(1), 24(2) offset about one hundred eighty degrees (180°) from one another around the circumference of the graft body 12. Each zigzag member 24 includes alternating loops, i.e., peaks 24a and valleys 24b alternating along the length of the loop region 20, that extend only partially around the circumference of the graft body 12, as shown in FIGS. 4A and 4B. The alternating loops of each zigzag member 24 may extend more than halfway around the circumference, i.e., greater than one hundred eighty degrees (180°), e.g., between about 180-300°, with the zigzag members 24 offset axially from one another by one loop such that the adjacent loops 24a, 24b of the zigzag members 24 nest at least partially between one another along the length of the loop region 20. For example, if each zigzag member 24 defines a 180° arc, the entire periphery may be covered; if each zigzag member 24 defines an arc greater than 180°, the zigzag members 24 may nest and overlap, thereby increasing the rigidity of the support provided.

Figure 4D:
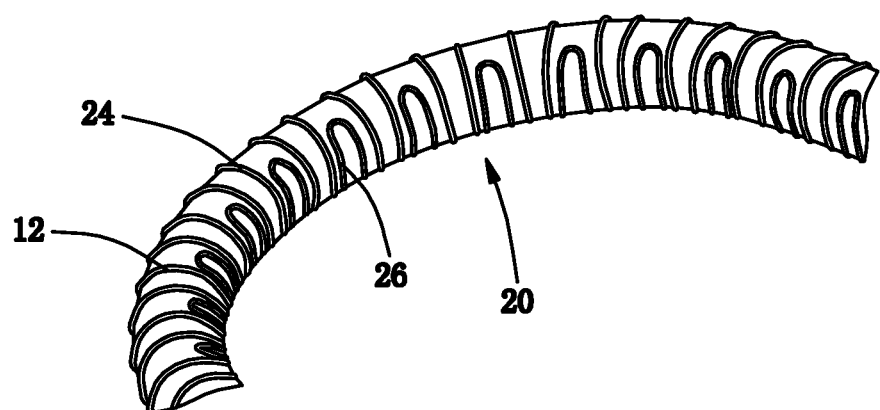
FIG. 4D is a perspective view of the loop region of FIGS. 4A-4C.

For example, as can be seen in FIG. 4C (a two-dimensional schematic of the zigzag members shown in FIGS. 4A and 4B), in this configuration, the peaks 24a(1) of the first zigzag member 24(1) may be axially aligned with adjacent valleys 24b(2) of the second zigzag member 24(2) along one side of the graft body 12 (i.e., above the axis 18, which is the central axis of curvature along the loop region 20), while the valleys 24b(1) of the first zigzag member 24(1) may be axially aligned with adjacent peaks 24a(2) of the second zigzag member 24(2) on the opposite side (i.e., below the axis 18). Thus, the zigzag members 24 may define a "clamshell" that wraps around the graft body 12 and partially interlock or overlap to support the graft body 12 in bending. Further, providing axial alignment of the loops 24a, 24b may create an axial "spine" 26 along one side of the graft body 12, which may have greater strut density and therefore provide greater support than an opposite side of the graft body 12. For example, as shown in FIG. 4D, the spine 26 may be positioned along an inner radius of the curve of the loop region 20 to provide greater support along the inside of the curve, which would otherwise be more likely to kink or buckle given axially compressive forces that may be encountered when the loop region 20 is bent. The side opposite the spine 26, e.g., positioned along an outer radius of the curve of the loop region, has less strut density and therefore may provide less support, but the outside of the curve may need less support, e.g., since the outside of the curve would subject to axially tensile forces when the loop region 20 is bent.

Although two zigzag members 24 are shown, alternatively, more than two zigzag members, e.g., three, four, or more (not shown), may be provided that extend axially along the cannulation region 30 that include alternating loops that extend around a portion of the circumference of the graft body 12. In this alternative, the zigzag members may be distributed around the circumference such that alternating loops of adjacent zigzag members partially overlap. For example, with four zigzag members, the alternating loops of each zigzag member may define an arc greater than one quarter of the circumference, i.e., greater than ninety degrees (90°), such that the peaks and valleys are nested between corresponding valleys and peaks of the circumferentially adjacent zigzag member.

Figure 5A:
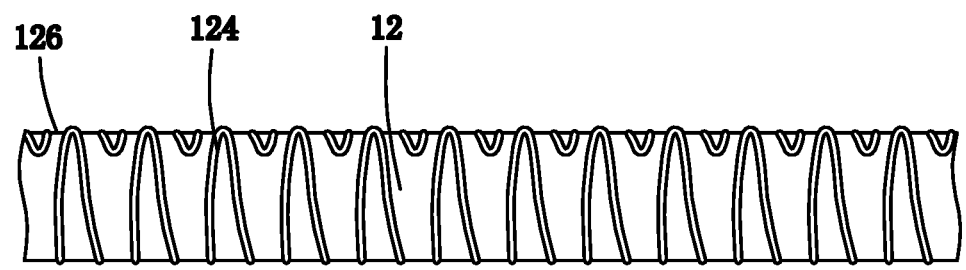
FIGS. 5A-5C are details showing another exemplary embodiment of reinforcement elements including a single zigzag element that extends along a loop region of a tubular graft, with alternating loops of the zigzag element wrapping entirely around the circumference of the loop region.
Figure 5B:
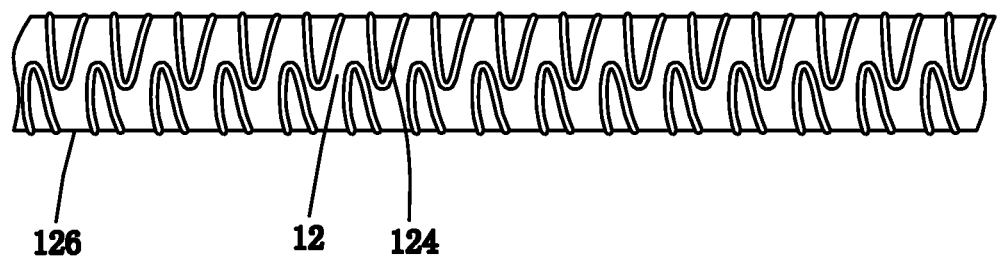
Figure 5C:
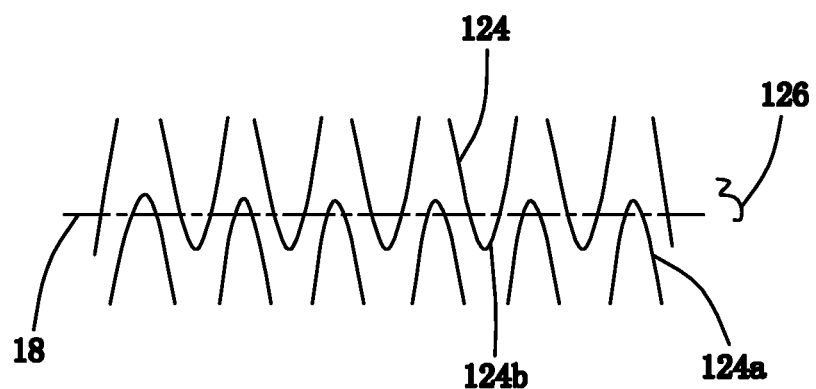

Alternatively, turning to FIGS. 5A-5C, the reinforcement element may include a single zigzag member 124 that extends partially or entirely around the circumference of the graft body 112 along the desired length of the loop region 20. For example, as can be seen in FIG. 5C (a two-dimensional schematic of the zigzag member 124 shown in FIGS. 5A and 5B), in this configuration, the upper loops 124*a* of the zigzag member 124 may be axially aligned with adjacent lower loops 124*b*. This axial alignment of the loops 124*a*, 124*b* may also create an axial "spine" 126 along one side of the graft body 12, which may have greater strut density and therefore provide greater support than an opposite side of the graft body 12.

For example, in one embodiment, the spine 126 may be positioned along an inner radius of the curve of the loop region 20 to provide greater support along the inside of the curve, as described above. Alternatively, as shown in FIG. 3, the spine 26 may be positioned at another circumferential location, e.g., between the inner and outer radius of the curve, e.g., offset about ninety degrees (90°) around the circumference from the inner radius of the curve.

In an exemplary embodiment, the zigzag member 124 may be formed by wrapping a plastic wire element or filament around a cylindrical mandrel (not shown), e.g., having an outer diameter similar to the outer diameter of the loop region 20. For example, a second smaller mandrel may be positioned adjacent the cylindrical mandrel, and a wire element for the zigzag member 124 may be wound partially around the cylindrical mandrel in a first circumferential direction until it is adjacent the smaller mandrel, whereupon the wire element may be wound around the smaller mandrel and then wrapped in a second circumferential direction around the cylindrical mandrel (opposite the first direction) until the wire element again reaches the smaller mandrel. The wire element may be wound around the smaller mandrel and wrapped in the first direction again, with this process being repeated as the wire element winds down the length of the cylindrical mandrel.

The wire element may be heat treated or otherwise processed to set the resulting shape into the wire element, whereupon the cylindrical and smaller mandrels may be removed to provide the zigzag member 124, which may then be attached to the graft body 12. For example, if the wire element is formed from nylon or other thermoplastic, hot air may be applied to the wire element/mandrels assembly to remove stress and/or set the shape into the zigzag member 124 before removing the mandrels. The zigzag member 124 may then be positioned around the graft body 112 and attached thereto along a desired length of the loop region, as described elsewhere herein. Alternatively, the smaller mandrel may remain interwoven with the wire element after removing the cylindrical mandrel, and the resulting zigzag member 124 may be positioned around and/or attached to the graft body 12, whereupon the smaller mandrel may be removed.

One advantage of axially oriented zigzag reinforcement elements is that the reinforcement elements may accommodate axial elongation or compression of the loop region 20, e.g., due to bending or other movement. If additional axial reinforcement is desired, the number of zigzag periods per unit length of the loop region 20 may be adjusted to provide a desired axial rigidity. Another advantage of zigzag reinforcement elements is that the asymmetrical geometry resulting from the zigzag pattern may provide a visual indicator of rotational orientation of the graft 10, e.g., under fluoroscopy or other external imaging, without the need to provide additional markers on the graft 10. For example, before introducing a needle or other device through the cannulation region 30, external imaging may be used to confirm the orientation of the reinforcement elements and/or loop region 20 to ensure that the needle is inserted through a supported region.

Figure 6A:
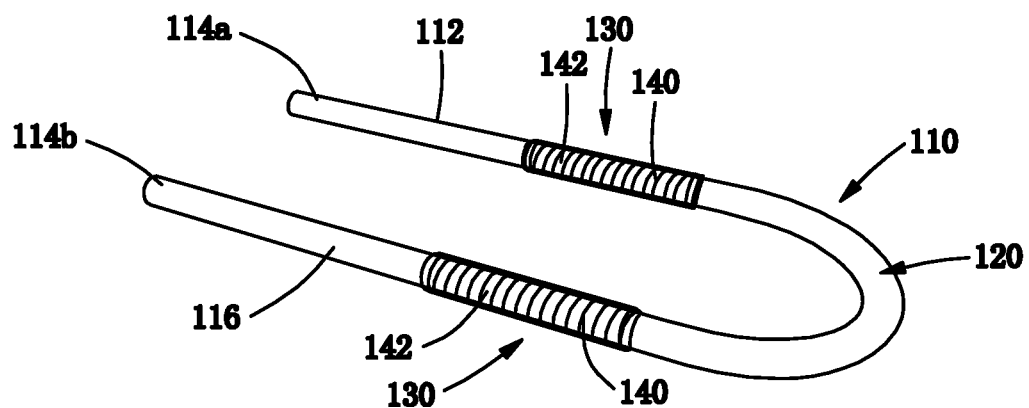
FIGS. 6A and 6B are perspective and top views, respectively, of another embodiment of a tubular graft including two self-sealing cannulation regions and a loop region between the cannulation regions.
Figure 6B:
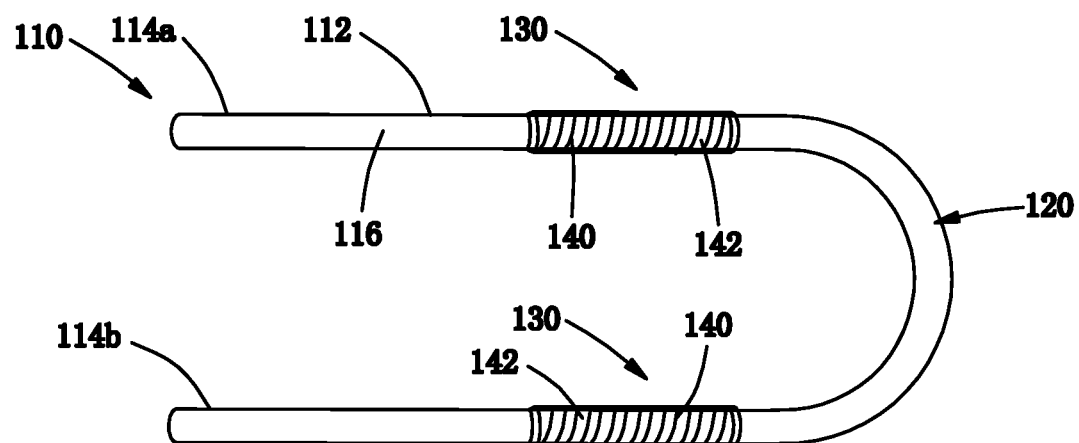
Figure 6C:
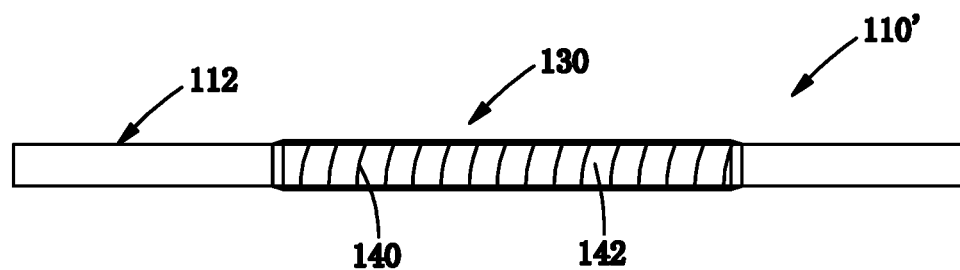
FIGS. 6C and 6D are side and cross-sectional views of yet another embodiment of a tubular graft including a single self-sealing cannulation region.
Figure 6D:
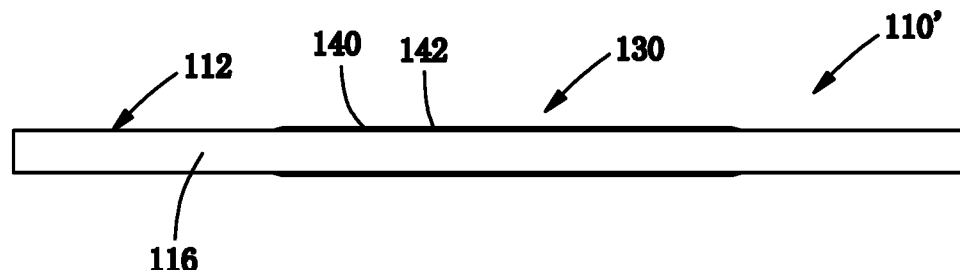

Turning to FIGS. 6A and 6B, another embodiment of a tubular graft 110 is shown that includes an intermediate loop region 120 and a pair of self-sealing cannulation regions 130 on either side of the loop region 120. Similar to the previous embodiments, the graft 110 includes an elongate tubular graft body 112 including first and second ends 114*a*, 114*b* and a lumen 116 extending between the ends 114*a*, 114*b*. Also similar to the previous embodiments, the loop region 120 may include one or more reinforcement elements (not shown). Alternatively, as shown in FIGS. 6C and 6D, a tubular graft 110' may be provided that includes a single cannulation region 130 on a tubular graft body 112, i.e., without a loop region.

Figure 6E:
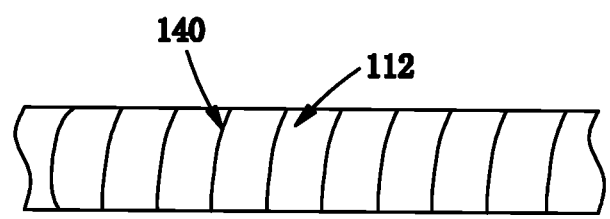
FIG. 6E is a detail showing an exemplary embodiment of a reinforcement element being embedded around an inner layer of a cannulation region of a tubular graft, such as those shown in FIGS. 6A-6C.
Figure 6F:
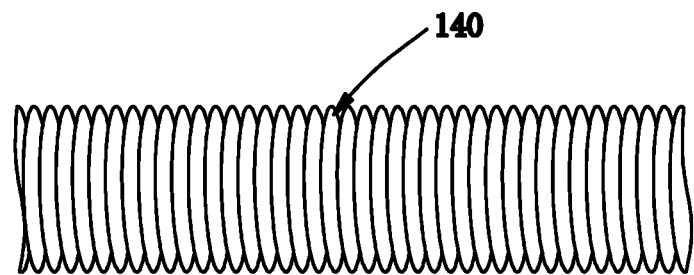
FIGS. 6F and 6G are details of the reinforcement element shown in FIG. 6E shown in a relaxed or low energy state (FIG. 6F) and a stretched state (FIG. 6G).
Figure 6G:
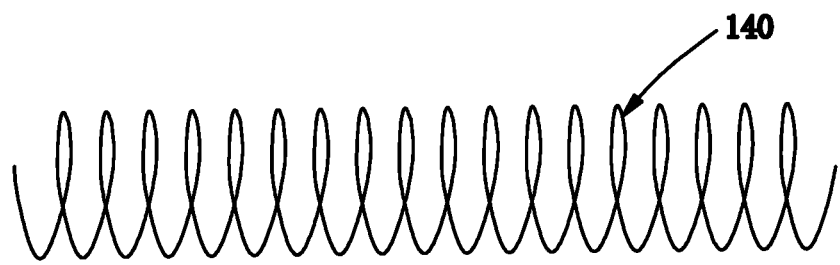

As shown, the cannulation region(s) 130 include one or more reinforcement elements 140 embedded in or surrounding base material 142, also similar to the previous embodiments. However, as shown in FIGS. 6E-6G, in this embodiment the reinforcement element is a helical coil 140 that extends around and along the cannulation region(s) 130. As can be seen in FIG. 6E, the helical coil 140 may be wrapped or otherwise positioned around the outer surface of the graft body 112 and then embedded within or surrounding the base material 142, e.g., silicone or other elastomeric material (not shown), similar to other embodiments herein and in the applications incorporated by reference herein. The helical coil 140 may be formed from metal, e.g., stainless steel, Nitinol, and the like, or other elastic or superelastic material, e.g., by laser cutting, mechanically cutting, stamping, machining, and the like, or from wire that may be formed into the spiral shape, similar to other embodiments herein.

Turning to FIGS. 6F and 6G, in an exemplary embodiment, the helical coil 140 may have a relaxed or low energy state in which adjacent coils contact one another with little or no gaps between the adjacent coils, e.g., as shown in FIG. 6F. During assembly, the helical coil 140 may be stretched longitudinally to create gaps or spaces between adjacent coils, e.g., having a substantially uniform or other desired spacing, as shown in FIG. 6G. The helical coil 140 may then be embedded within or around base material (not shown) to provide a self-sealing structure. When the helical coil 140 is released after being embedded in the base material, the helical coil 140 will be biased to return to its low energy state. Consequently, the helical coil 140 may apply a primarily axially compressive force to the base material (and to the underlying graft body 112 given the compressive force and greater stiffness of the helical coil 140 compared to the material of the graft body 112), which may enhance sealing when a needle or other device is introduced through the structure. Optionally, the helical coil 140 may be sized to apply a radially compressive force to the base material 142, e.g., by sizing the helical coil 140 to have a relaxed or low energy diameter smaller than the graft body 112. In another alternative, the helical coil 140 may be embedded within the base material 142 in a relaxed and/or other low energy state, e.g., such that the helical coil 140 does not impose a radial and/or axial compressive force to the base material 142. Such a configuration may provide support for the internal lumen 116 of the graft body 112, e.g., to prevent the lumen 116 from being crushed when external pressure is applied, e.g., externally to the patient's skin overlying the graft 110.

In an exemplary embodiment, the base material may be formed directly around the graft body 112 and helical coil 140, e.g., by placing the helical coil 140 (in its stretched and/or radially expanded state) and desired length of the graft body 112 within a cavity of a mold and filling the cavity with base material. Alternatively, one or more layers of base material, e.g., in sheet or tubular form, may be wrapped, slid, or otherwise applied around the graft body 112, e.g., a first layer between the helical coil 140 and the graft body 112 and a second layer over the helical coil 140 (not shown). The base material may be cured, heated, and/or otherwise processed to embed the helical coil 140 within the base material and/or to attach the base material and helical coil 140 to the graft body 112. Optionally, an outer layer (not shown) may be applied over the base material after curing, e.g., an ePTFE sleeve similar to that shown in FIG. 2B and/or fabric may be applied over exposed surfaces to provide a desired finish for the cannulation region 30.

In a further alternative, the helical coil 140 may be embedded (again in its stretched state) within base material formed into a tubular sleeve, and then applied over and substantially permanently attached to the graft body 112, e.g., by bonding with adhesive, fusing, and the like, as described in the applications incorporated by reference herein. Optionally, in this alternative, fabric may be applied over exposed surfaces before attaching the sleeve to the graft body 112 or an outer layer (not shown) may be applied over the sleeve after attachment to the graft body 112. Additional information regarding methods for forming a cannulation region including the helical coil 140 embedded within base material may be found in the applications incorporated by reference herein.

Figure 7A:
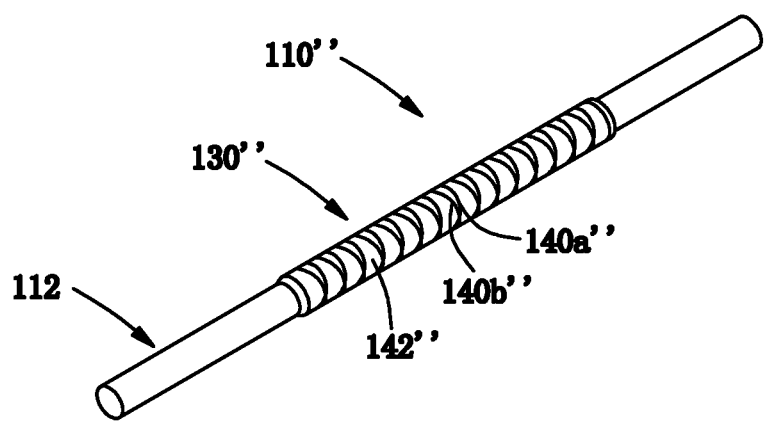
FIGS. 7A-7C are perspective, side, and cross-sectional views, respectively, of still another embodiment of a tubular graft including a single self-sealing cannulation region.
Figure 7B:
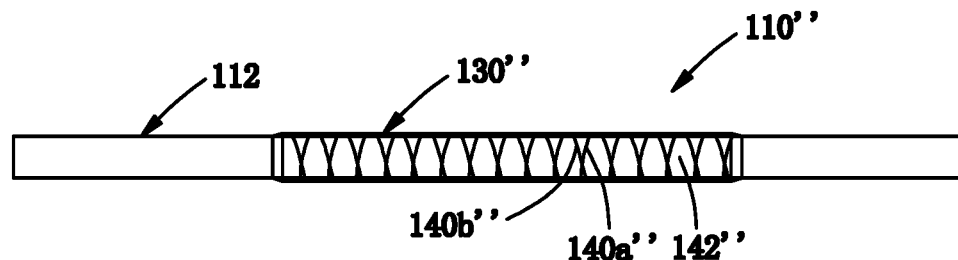
Figure 7C:
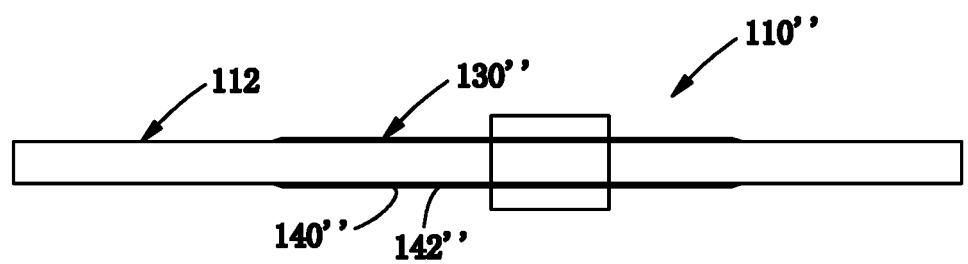
Figure 7D:
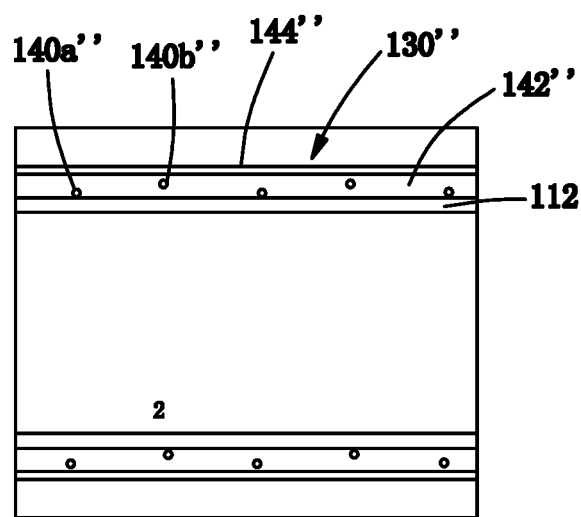
FIG. 7D is a detail of the cross-section of the tubular graft of FIG. 7C.

In other alternatives, multiple stretched helical coils may be embedded within base material (and subsequently released) to provide the cannulation region. For example, FIGS. 7A-7C show another embodiment of a tubular graft 110" that includes a cannulation region 130" on a graft body 112, including first and second helical coils 140a," 140b" embedded within base material 142." Optionally, the cannulation region 130" may include an outer sleeve 144" and/or fabric covering, similar to other embodiments herein. As best seen in FIGS. 7A and 7B, the first helical coil 140a" has windings extending in a first helical direction, and the second helical coil 140b" has windings extending in a second helical direction opposite the first direction. In addition, as shown in FIG. 7D, the second helical coil 140b" has a diameter greater than the first helical coil 140a" such that the second helical coil 140b" may be positioned concentrically around the first helical coil 140a" (i.e., without braiding the helical coils together). In one embodiment, the diameters may be set such that the second helical coil 140b" may contact the first helical coil 140a" at overlap points, or, alternatively, the second helical coil 140b" may be spaced apart from the first helical coil 140a" such that base material 142" flows or is otherwise located between the helical coils 140" to space them apart from one another. This configuration may provide more uniform axial compression along the cannulation region 130" since any torsional forces between the helical coils may cancel each other out. In addition or alternatively, the overlapping helical coils 140" may provide a more uniform outer surface, e.g., preventing the base material 142" from bulging outwardly between the helical coils 140."

Figure 8A:
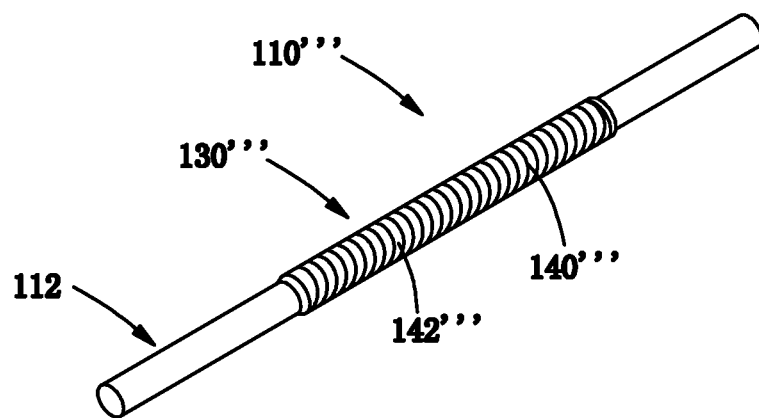
FIGS. 8A-8C are perspective, side, and cross-sectional views, respectively, of yet another embodiment of a tubular graft including a single self-sealing cannulation region.
Figure 8B:
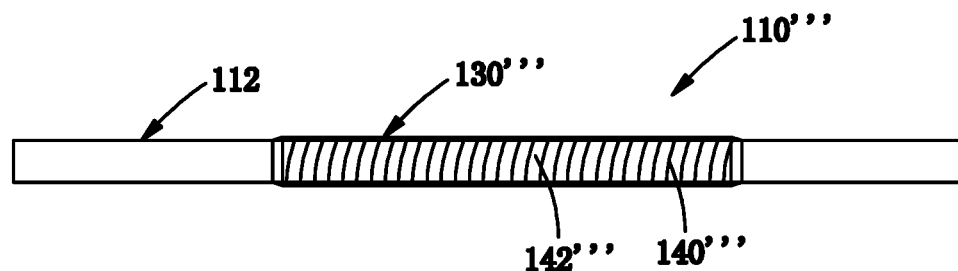
Figure 8C:
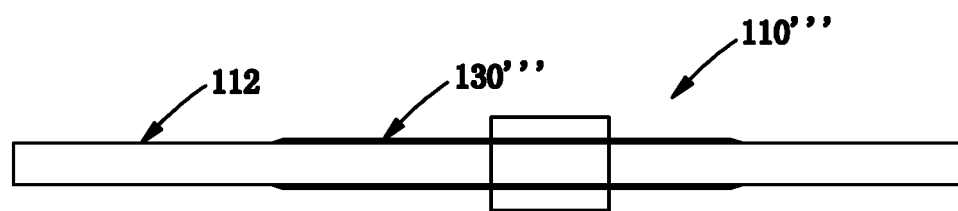
Figure 8D:
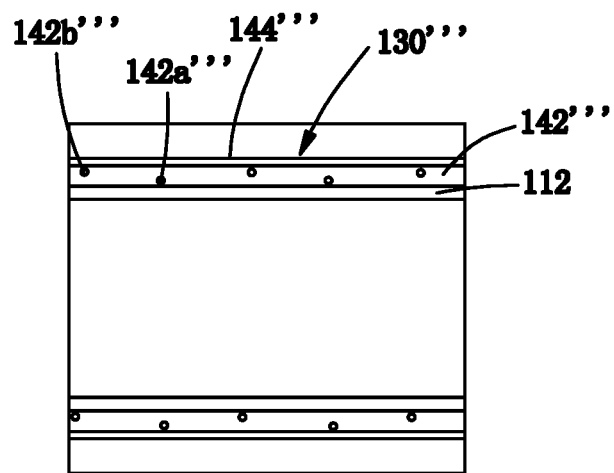
FIG. 8D is a detail of the cross-section of the tubular graft of FIG. 8C.

Turning to FIGS. 8A-8C, in another alternative, a cannulation region 130'" may be provided on a tubular graft 110'" that includes two helical coils 140'" with windings that extend in the same helical direction, i.e., with a second helical coil 140b'" disposed concentrically around a first helical coil 140a'" as shown in FIG. 8D. In this alternative, the windings of the second helical coil 140b'" may be axially aligned with windings of the first helical coil 140a'" (in phase) or they may be offset from one another (out of phase), as desired. Alternatively, two (or more) helical coils may be embedded together within the base material that have the same relaxed diameter but are offset axially from one another, e.g., by a half period or other desired spacing.

Returning to FIGS. 6A-6C, a tubular graft 110 may be implanted within a patient's body, e.g., within the patient's forearm to provide arterial and venous access via cannulation regions 130 (including one or more helical coils 140 embedded in base material 142). When it is desired to access the lumen 116 of the graft 110, a needle and/or other device (not shown) may be introduced through the patient's skin overlying the graft 110, and directed through one of the cannulation regions 130 into the lumen 116. Where the cannulation region 130 includes a helical coil 140, as shown in FIG. 6A (or multiple coils 140" or 140'" as shown in FIG. 7A-7C or 8A-8C), the needle may pass through one of the gaps between the spaced apart windings into the lumen of the graft body 112. Optionally, the helical coil(s) 140 (140," 140'") may have a rounded or other cross-section to facilitate the device passing between adjacent windings. When the needle or other device is removed, the axial compressive force applied by the helical coil(s) 140 (140," 140'") may bias the base material 142 (142," 142'") to close the puncture site, thereby maintaining a substantially fluid-tight seal in the wall of the tubular graft 110 (110," 110'"). In addition, the helical coil(s) 140 (140," 140'") may prevent accidental leakage from graft 110, e.g., subcutaneous or subdermal bleeding resulting from infiltration, if the needle is accidentally inserted entirely through the graft body 112 and out the opposite side of the cannulation region 130 since the helical coil(s) 140 also applies an axial compressive force along the posterior side of the cannulation region 130.

Figure 9A:
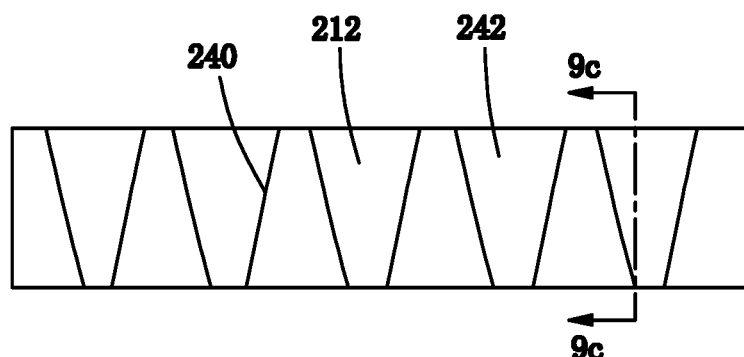
FIGS. 9A and 9B are side views of an exemplary embodiment of a cannulation region of a tubular graft including a reinforcement element that extends partially around a circumference of an elastomeric layer into which the reinforcement element is embedded.
Figure 9B:
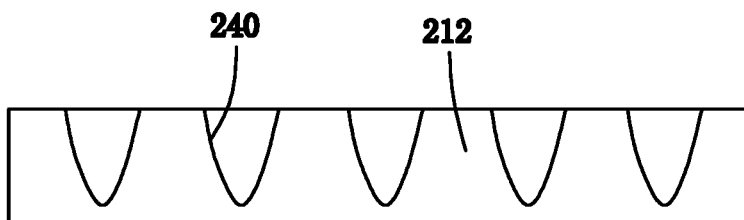
Figure 9C:
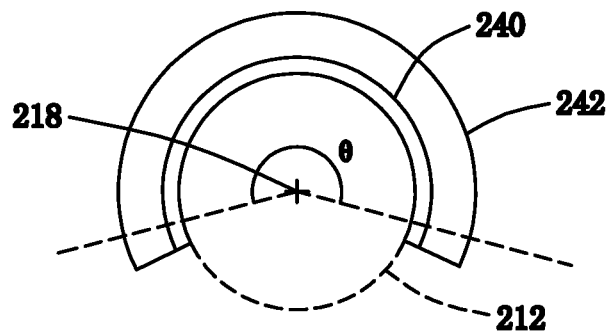
FIG. 9C is a cross-sectional view of the cannulation region of FIG. 9A taken along plane 9C-9C.
Figure 9D:
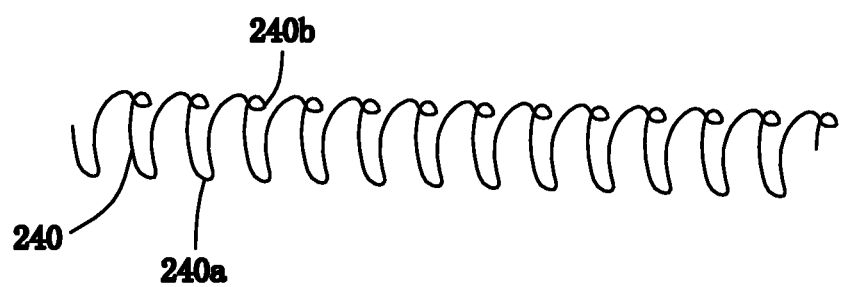
FIG. 9D shows an exemplary embodiment of a reinforcement element that may be embedded in the cannulation region of FIGS. 9A-9C.

Turning to FIGS. 9A-9D, still another embodiment of a reinforcement member is shown, namely a zigzag member 240 that extends along the length of a cannulation region of a tubular graft (or alternatively, the zigzag member 240 may be embedded in base material for a patch, similar to other embodiments herein), such as the cannulation regions 30 shown in FIG. 1. As can be seen in FIGS. 9A-9C, the zigzag member 240 may be wrapped or otherwise positioned around the outer surface of a tubular graft body 212 and then embedded within or surrounding base material 242, e.g., silicone or other elastomeric material, similar to other embodiments herein and in the applications incorporated by reference herein. As best seen in FIG. 7D, the zigzag member 240 includes alternating loops (e.g., peaks 240a and valleys 240b) that extend at least partially around the circumference of the graft body 212 and alternate along the length of the cannulation region. Thus, the loops 240a, 240b may define an arc orthogonal to the longitudinal axis 218 corresponding to an outer diameter of the graft body 212 with the arc length being a predetermined portion of the entire circumference.

For example, FIG. 9C shows a cross-section of the zigzag member 240 embedded in base material 242 that extends only partially around the circumference of the graft body 212 (shown in phantom), e.g., thereby defining an arc angle θ, e.g., between about 180-360° or between about 180-300°, around the circumference. In this embodiment, the resulting cannulation region may only extend partially around the device body 212 and so, during implantation, the resulting tubular graft 10 may be implanted to orient the cannulation region anteriorly, i.e., towards the skin through which the cannulation region would be accessed.

Figure 10A:
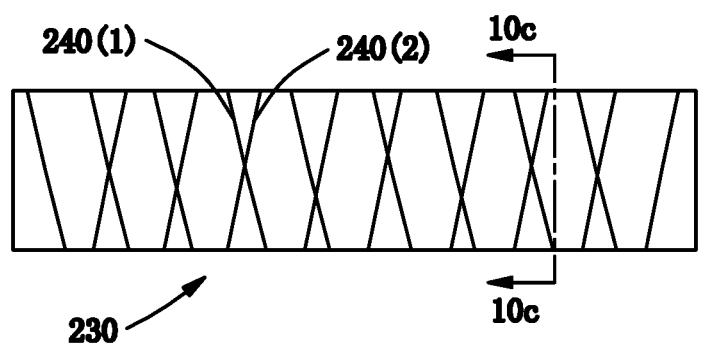
FIGS. 10A and 10B are side views of another exemplary embodiment of a cannulation region of a tubular graft including a pair of overlapping reinforcement elements that extend partially around a circumference of an elastomeric layer into which the reinforcement element is embedded.
Figure 10B:
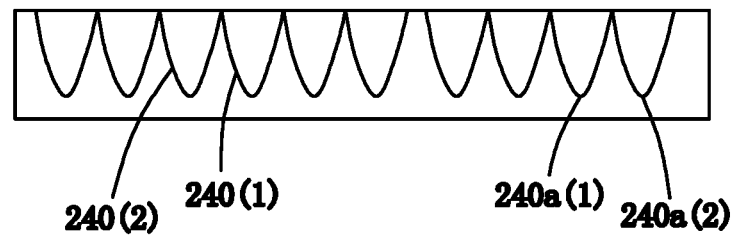

Turning to FIGS. 10A-10D, another embodiment is shown that includes a pair of reinforcement members 240 (1), 240(2) embedded within base material 242 and attached around a tubular graft body 212 to provide a cannulation region 230 (or embedded within base material for a patch, similar to other embodiments herein). Each reinforcement member 240 may be formed as a zigzag member similar to that shown in FIG. 9D, i.e., including alternating loops (e.g., peaks 240a and valleys 240b) that extend at least partially around the circumference of the graft body 212 and alternate along the length of the cannulation region. Alternatively, one or both zigzag member 240 may define a more complicated repeating pattern, e.g., having a shape similar to the zigzag member 340 shown in FIG. 11, which defines nonlinear peaks 340a and valleys 340b. This alternative may provide the ability to alter the amount of compression along the arc of the pattern or influence the final geometry of the lumen. For example, more complicated shapes may allow for controlling the degree of compression in any location along the cannulation region 230 and/or control the specific geometry of the areas not covered by the zigzag member 340 to facilitate minimized contact between a needle and the zigzag member 340.

Figure 10C:
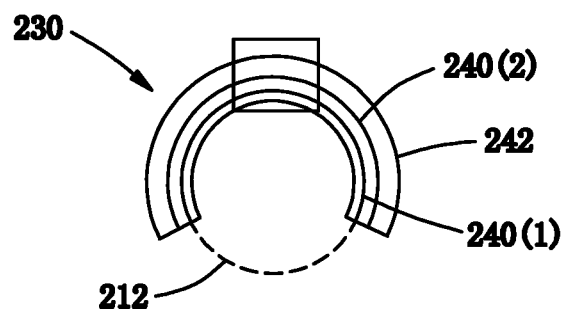
FIG. 10C is a cross-sectional view of the cannulation region of FIG. 10A taken along plane 10C-10C.
Figure 10D:
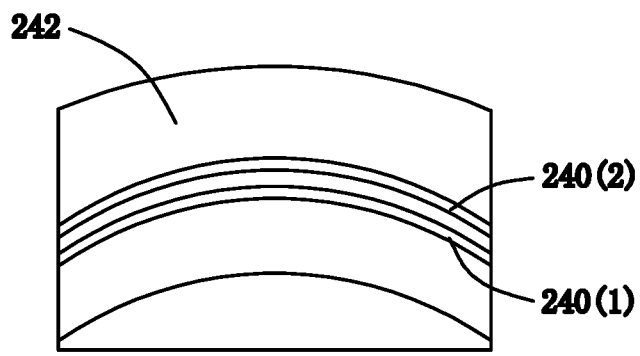
FIG. 10D is a detail showing a spacing between the overlapped reinforcement elements shown in FIGS. 10A-10C.
Figure 11:
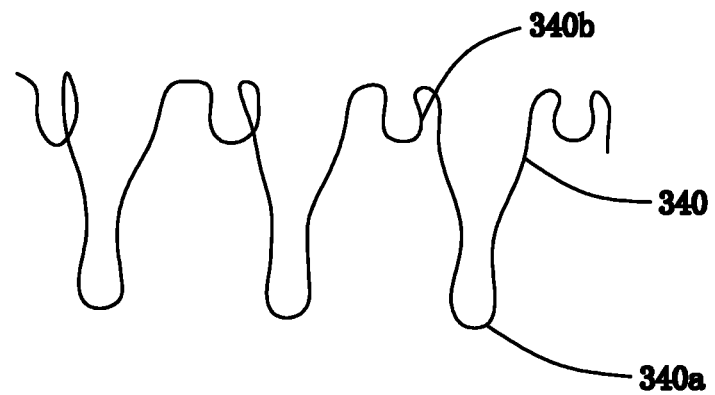
FIG. 11 is a detail showing another exemplary embodiment of a reinforcement element that may be embedded in the cannulation region of a tubular graft, such as that shown in FIGS. 9A-9C and 10A-10C.

As can be seen in FIGS. 10C and 10D, the first zigzag member 240(1) defines a first radius of curvature that is larger than the outer diameter of the graft body 212 and the second zigzag member 240(2) defines a second radius of curvature that is larger than the first radius such that the second zigzag member 240(2) is spaced apart radially outwardly from the first zigzag member 240(1), e.g., by a desired distance δ between about zero and five millimeters (0-5.0 mm). Alternatively, the zigzag members 240 may be biased to the same diameter but may be offset axially from one another, e.g., by half a period or other desired spacing.

In addition, as can be seen in FIGS. 10A and 10B, the zigzag members 240 may be offset axially from one another, e.g., by half a period, such that the peaks and valleys are spaced uniformly along the cannulation region. Providing overlapping zigzag members 240 may provide more uniform compressive forces to the base material 242, may reduce bulging, and/or may provide greater wire density to the base material 242, which may enhance self-sealing of the cannulation region after being punctured, similar to other embodiments described elsewhere herein. In addition, having inner and outer zigzag members 240 may provide more uniform compressive, i.e., sealing forces, through the thickness of the base material 242.

Optionally, the properties of the inner and outer zigzag members 240 may be varied, i.e., with the outer zigzag member 240(2) having different elasticities, thicknesses, and/or other mechanical properties, e.g., to provide different compliances between the zigzag members 240, which may vary the properties towards the inner and outer surfaces of the cannulation region 230. For example, depending on where the neutral axis is along the cannulation region, greater or lesser compression by the inner and/or outer members 240 may keep the cannulation region 230 from bowing or bending in an undesirable manner. In addition or alternatively, the shape and/or other mechanical properties of the zigzag members 240 may be varied along their lengths, e.g., to provide different compliances and/or other properties along the length of the cannulation region 230.

Turning to FIGS. 12A-12F, an exemplary embodiment of a self-sealing patch 430 is shown that includes a plurality of reinforcement elements 440 embedded within base material 442, e.g., similar to the cannulation regions described above. Generally, the patch 430 is an elongate body including first and second ends 432 and defining a "C" shaped cross-section that includes opposing side edges 434 extending between the opposite ends 432, thereby defining an inner lumen or recess 436.

Figure 12A:
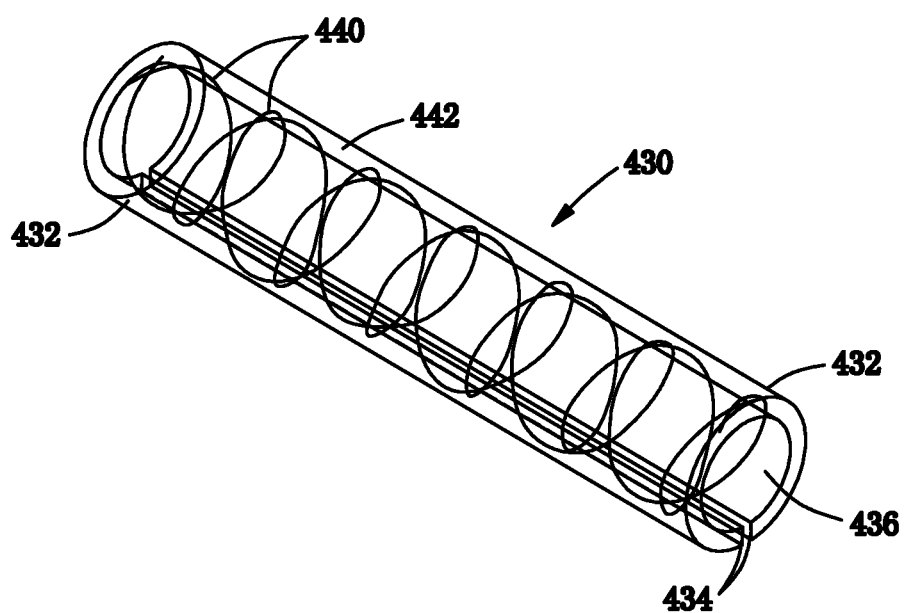
FIGS. 12A-12D are perspective, top side, and bottom views, respectively, of an exemplary embodiment of a self-sealing patch including a pair of reinforcement elements.
Figure 12B:
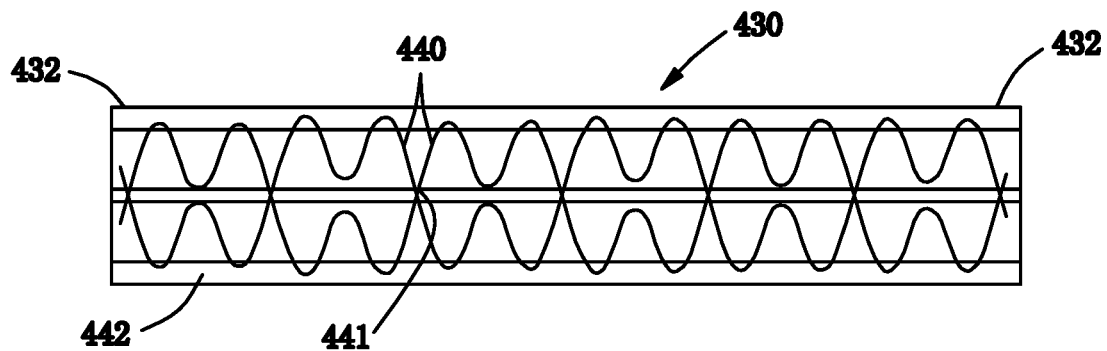
Figure 12C:
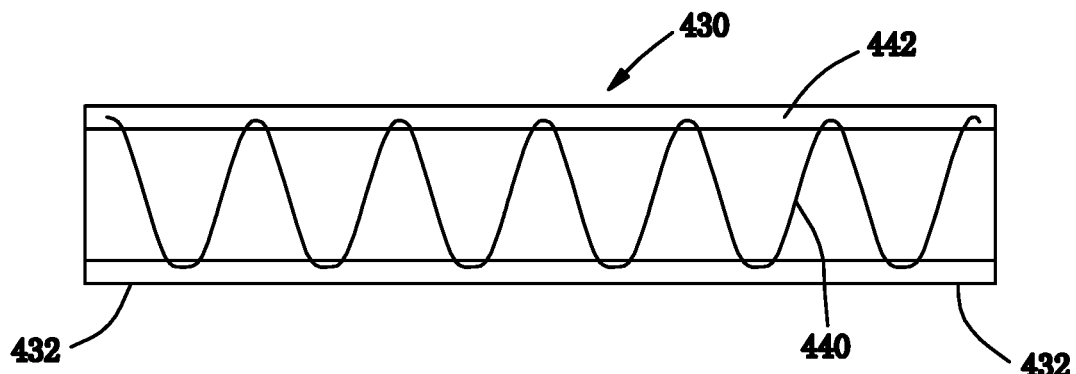
Figure 12D:
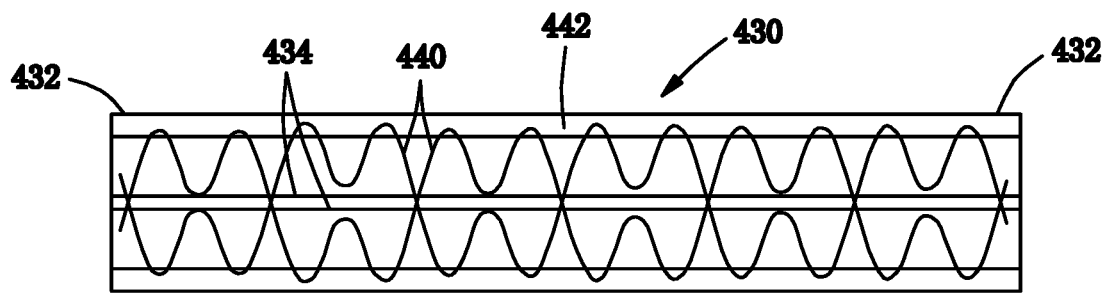
Figure 12E:
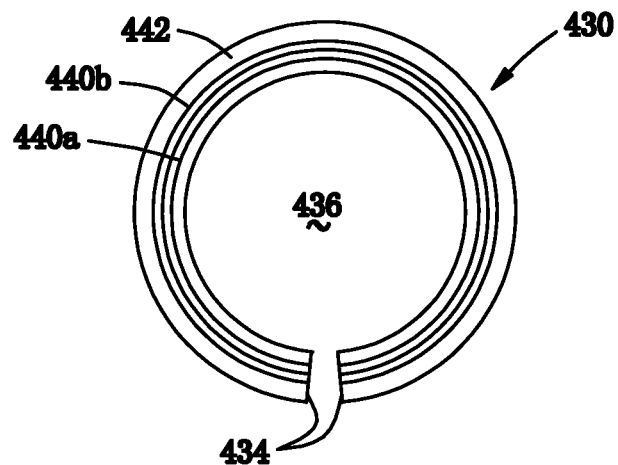
FIG. 12E is an end view of the patch of FIGS. 12A-12D.
Figure 12F:
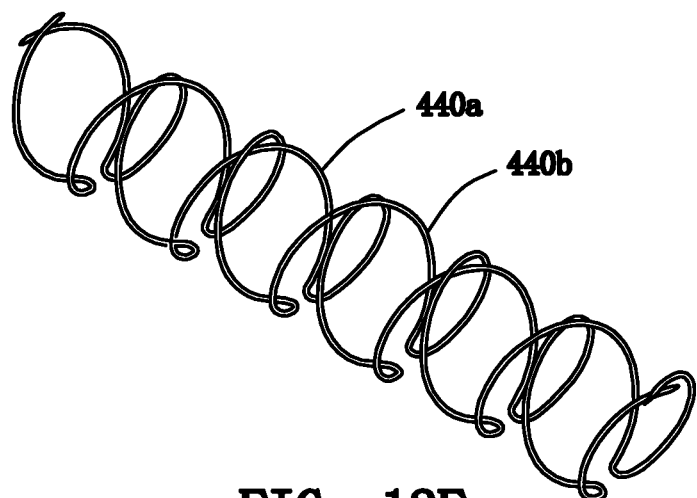
FIG. 12F is a perspective view of the reinforcement elements of the patch of FIGS. 12A-12D.

As best seen in FIG. 12E, the patch 430 may be formed as a cuff, defining an arc greater than one hundred eighty degrees (180°), e.g., between about 180-360° or between about 180-300°, sized to receive a tubular structure (not shown) within the recess 436. Alternatively, the patch 430 may have a substantially planar or curved shape (not shown), e.g., such that an inner surface of the patch 430 may be attached to a tissue or other body structure, as described in the applications incorporated by reference herein. For example, the reinforcement elements 440 and base material 442 may be sufficiently flexible such that the side edges 434 may be separated to allow the patch 430 to be positioned over and around a tubular structure, such as a tubular graft (not shown), e.g., similar to the grafts described elsewhere herein and in the applications incorporated by reference herein.

As best seen in FIG. 12E, the reinforcement elements 440 include an inner zigzag member 440a and an outer zigzag member 440b. Each zigzag member 440 may include alternating loops (e.g., peaks and valleys) that extend at least partially around the circumference of the patch 430 and alternate along a desired length of the patch 430. In the embodiment shown, adjacent peaks and valleys of each zigzag member 440 are spaced apart axially, and the zigzag members 440 are offset axially from one another such that the peaks of one zigzag member 440a along one side edge 434 are axially aligned with the valleys of the other zigzag member 440b on the opposite side edge 434.

Similar to previous embodiments, the outer member 440b may have a larger diameter than the inner member 440a such that the outer member 440b may be disposed concentrically around the inner member 440a (i.e., without braiding or otherwise overlapping the inner member 440a over the outer member 440b). In addition, the outer member 440b may be spaced apart from the inner member 440a, i.e., such that base material 442 is disposed between the members 440, or, the outer member 440b may contact the inner member 440a, e.g., at overlap points 441 at the top of the patch 430, best seen in FIG. 12B.

Turning to FIGS. 13A-13F, another exemplary embodiment of a self-sealing patch 530 is shown that includes a plurality of reinforcement elements 540 embedded within base material 542. Generally, similar to the patch 430, the patch 530 is an elongate body including first and second ends 532 and defining a "C" shaped cross-section that includes opposing side edges 534 extending between the opposite ends 532, thereby defining an inner lumen or recess 536. Optionally, as shown, the side edges 534 may be beveled and/or rounded at the ends 532, e.g., to facilitate positioning the patch 530 over a tubular structure.

Figure 13A:
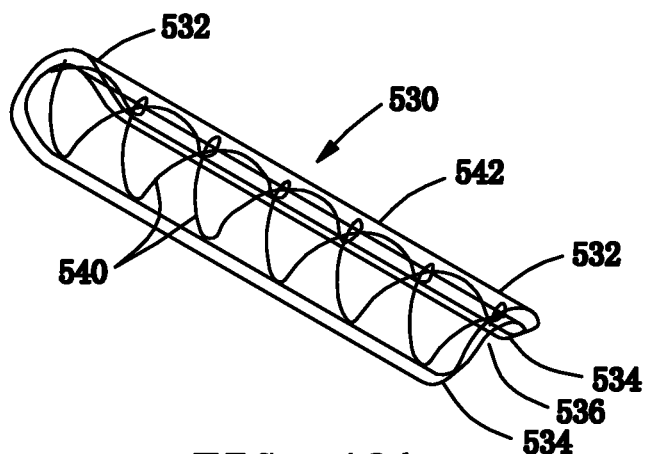
FIGS. 13A-13D are perspective, top side, and bottom views, respectively, of another exemplary embodiment of a self-sealing patch including a pair of reinforcement elements.
Figure 13B:
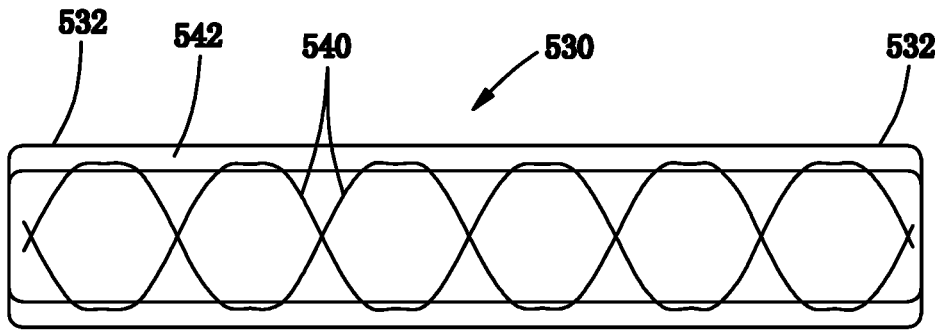
Figure 13C:
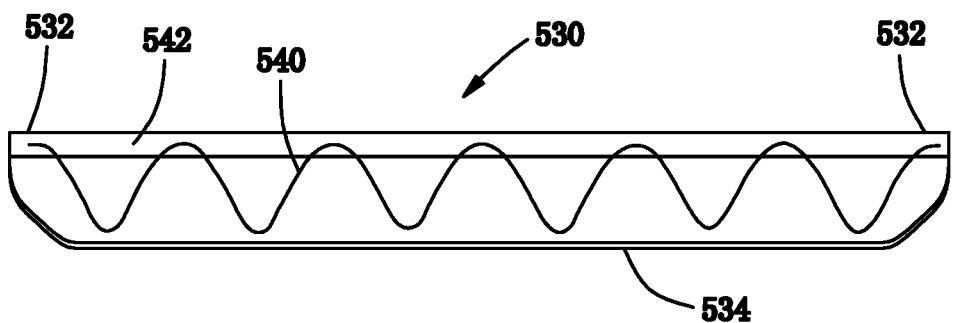
Figure 13D:
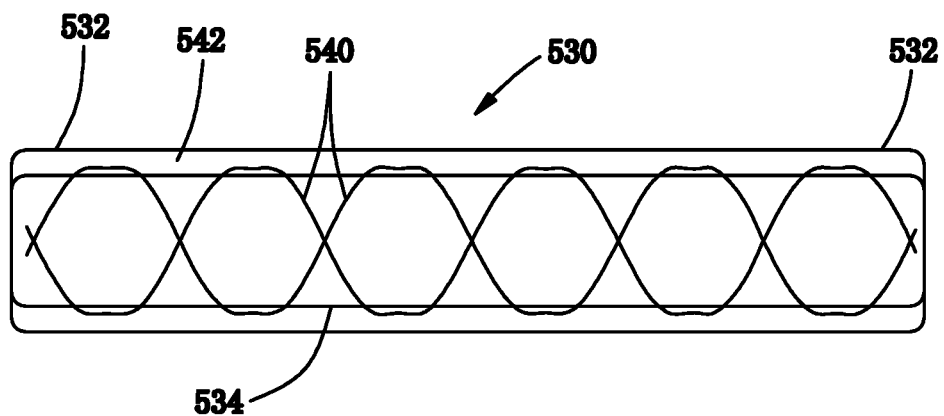
Figure 13E:
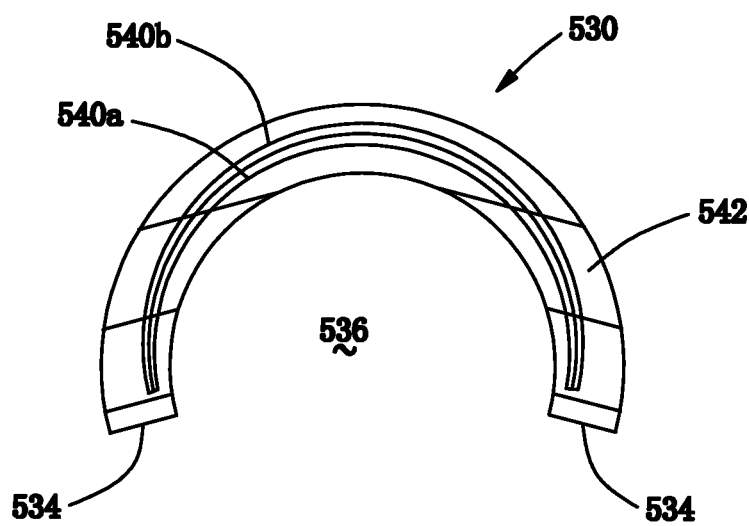
FIG. 13E is an end view of the patch of FIGS. 13A-13D.
Figure 13F:
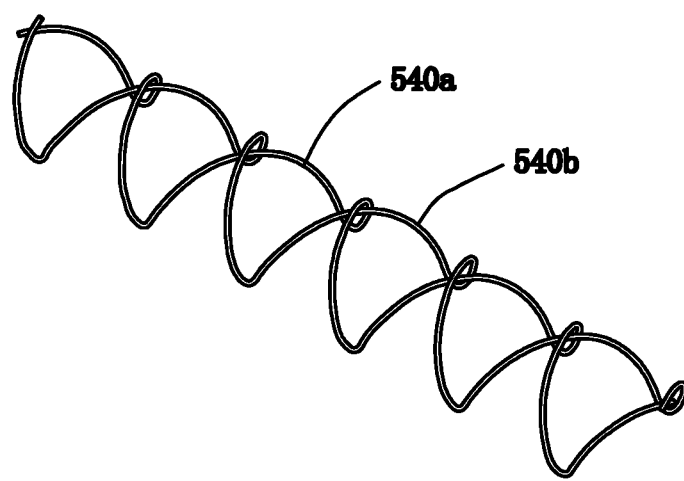
FIG. 13F is a perspective view of the reinforcement elements of the patch of FIGS. 13A-13D.

In this embodiment, the reinforcement elements 540 also include an inner zigzag member 540a and an outer zigzag member 540b disposed concentrically around the inner member 540a. As best seen in FIG. 13E, each zigzag member 540 may include alternating loops (e.g., peaks and valleys) that extend at least partially around the circumference of the patch 530 and alternate along a desired length of the patch 530, similar to the previous embodiments. In this embodiment, the arc of the patch 530 is smaller than that of the patch 430 and the zigzag members 540 have shorter circumferential amplitudes along the length of the patch 530 than the zigzag members 440. It will appreciated that the shape and/or period of the zigzag members 440, 540 may be varied to provide desired compliances and/or other mechanical properties, as described previously for other reinforcement elements.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the devices described herein may be combined with any of the delivery systems and methods also described herein.

While embodiments of the present invention have been shown and described, various modifications may be made without departing from the scope of the present invention. The invention, therefore, should not be limited, except to the following claims, and their equivalents.

We claim:

1. A self-sealing cuff, comprising:
    base material defining a first end, a second end, and having a "C" shaped cross-section defining opposing edges extending between the first and second ends; and
    first and second reinforcement members embedded within the base material, the first reinforcement member extending axially along a first length and including elements that extend at least partially around a circumference of the base material, the second reinforcement member extending axially along the first length and including elements that extend at least partially around the circumference of the base material, the second reinforcement member disposed concentrically around and spaced apart radially from the first reinforcement member along the first length; and wherein base material is located between the radially spaced apart first and second reinforcement members.

2. The cuff of claim 1, wherein the first and second reinforcement members comprise first and second zigzag members that extends axially along the first length and include alternating loops defining peaks and valleys that extend at least partially around the circumference of the tubular body.

3. The cuff of claim 2, wherein the first and second zigzag members are out of phase with one another such that peaks of the first zigzag member are disposed opposite valleys of the second zigzag member along the opposite side edges.

4. The cuff of claim 2, wherein the first and second zigzag members are out of phase with one another such that the second zigzag member overlaps the first zigzag member.

5. The cuff of claim 2, wherein the "C" shaped cross-section defines an arc greater than one hundred eighty degrees (180°).

6. The cuff of claim 2, wherein the "C" shaped cross-section defines an arc between about 180-300°.

7. The cuff of claim 2, wherein the peaks of the first zigzag member are disposed adjacent a first side edge of the opposing edges and the valleys of the second zigzag member are disposed adjacent a second side of the opposing edges opposite the peaks of the first zigzag member.

8. The cuff of claim 2, wherein the peaks of the first and second zigzag members alternate along a first side edge of the opposing edges and the valleys of the first and second zigzag members alternative along a second side edge of the opposing edges.

9. The cuff of claim 2, wherein the second zigzag member overlies and intersects the first zigzag member at intermediate locations between the peaks and valleys.

10. The cuff of claim 1, wherein the first and second reinforcement members are configured to apply axially compressive forces to the base material between the first and second ends.

11. The cuff of claim 1, wherein the first and second reinforcement members do not contact one another.

12. The cuff of claim 1, further comprising fabric applied over exposed surfaces of the base material.

13. A self-sealing cuff, comprising:
    base material defining a first end, a second end, and having a "C" shaped cross-section defining opposing edges extending between the first and second ends;
    first and second zigzag members embedded within the base material; and
    fabric applied over exposed surfaces of the base material;
    wherein the first zigzag member extends axially along a first length and includes elements that extend at least partially around a circumference of the base material, the second zigzag member extends axially along the first length and includes elements that extend at least partially around the circumference of the base material,
    wherein the first and second zigzag members are out of phase with one another such that peaks of the first zigzag member are disposed opposite valleys of the second zigzag member along the opposite side edges, the second zigzag member spaced apart radially from the first zigzag member such that base material is located between the first and second zigzag members.

14. The cuff of claim 13, wherein the second zigzag member overlies and intersects the first zigzag member at intermediate locations between the peaks and valleys.

15. The cuff of claim 13, wherein the fabric is applied over outer, inner, and end surfaces of the base material.

16. A self-sealing cuff, comprising:
    base material defining a first end, a second end, and having a "C" shaped cross-section defining opposing edges extending between the first and second ends; and
    inner and outer zigzag members embedded within the base material;
    wherein the inner zigzag member extends axially along a first length and includes elements that extend at least partially around a circumference of the base material, the outer zigzag member extends axially along the first length and includes elements that extend at least partially around the circumference of the base material,
    wherein the inner and outer zigzag members are out of phase with one another such that peaks of the inner zigzag member are disposed opposite valleys of the outer zigzag member along the opposite side edges, the outer zigzag member disposed concentrically around and spaced apart radially from the inner zigzag member along the first length; and wherein base material is located between the radially spaced apart first and second reinforcement members.

17. The cuff of claim 16, further comprising fabric applied over exposed surfaces of the base material.

18. The cuff of claim 16, wherein the inner and outer zigzag members do not contact one another.

* * * * *